United States Patent
Rios et al.

(10) Patent No.: US 10,650,703 B2
(45) Date of Patent: May 12, 2020

(54) SUTURE TECHNIQUE TRAINING SYSTEM

(71) Applicant: Truinject Corp., Newport Beach, CA (US)

(72) Inventors: Gabrielle A. Rios, Newport Beach, CA (US); Clark B. Foster, Mission Viejo, CA (US)

(73) Assignee: Truinject Corp., Newport Beach, CA (US)

( * ) Notice: Subject to any disclaimer, the term of this patent is extended or adjusted under 35 U.S.C. 154(b) by 305 days.

(21) Appl. No.: 15/865,833

(22) Filed: Jan. 9, 2018

(65) Prior Publication Data

US 2018/0197441 A1 Jul. 12, 2018

Related U.S. Application Data

(60) Provisional application No. 62/444,483, filed on Jan. 10, 2017.

(51) Int. Cl.
| | | |
|---|---|---|
| *G09B 23/28* | (2006.01) | |
| *G09B 23/30* | (2006.01) | |
| *A61B 17/04* | (2006.01) | |
| *A61B 17/34* | (2006.01) | |
| *A61B 17/06* | (2006.01) | |
| *G09B 9/00* | (2006.01) | |

(52) U.S. Cl.
CPC .............. *G09B 23/28* (2013.01); *A61B 17/04* (2013.01); *A61B 17/0469* (2013.01); *A61B 17/0482* (2013.01); *A61B 17/06166* (2013.01); *A61B 17/3403* (2013.01); *G09B 23/285* (2013.01); *G09B 23/30* (2013.01); *G09B 9/00* (2013.01)

(58) Field of Classification Search
None
See application file for complete search history.

(56) References Cited

U.S. PATENT DOCUMENTS

| | | |
|---|---|---|
| 3,941,121 A | 3/1976 | Olinger et al. |
| 4,142,517 A | 3/1979 | Contreras Guerrero de Stavropoulos et al. |
| 4,311,138 A | 1/1982 | Sugarman |
| 4,356,828 A | 11/1982 | Jamshidi |

(Continued)

FOREIGN PATENT DOCUMENTS

| | | |
|---|---|---|
| CN | 102708745 A | 10/2012 |
| EP | 0316763 A1 | 5/1989 |

(Continued)

OTHER PUBLICATIONS

Afzal, et al., "Use of Earth's Magnetic Field for Mitigating Gyroscope Errors Regardless of Magnetic Perturbation," Sensors 2011, 11, 11390-11414; doi:10.3390/s111211390, 25 pp. published Nov. 30, 2011.

(Continued)

*Primary Examiner* — Jason T Yen
(74) *Attorney, Agent, or Firm* — Knobbe, Martens, Olson & Bear, LLP

(57) ABSTRACT

Systems and methods are disclosed for practicing suturing techniques on a training apparatus using a training tool. The training apparatus can include a three-dimensional tracking system to detect a position of the training tool. A processing unit can process the positional data to determine one or more performance parameters. The performance parameters can be output to a display.

20 Claims, 4 Drawing Sheets

(56) References Cited

U.S. PATENT DOCUMENTS

| | | |
|---|---|---|
| 4,410,020 A | 10/1983 | Lorenz |
| 4,515,168 A | 5/1985 | Chester et al. |
| 4,566,438 A | 1/1986 | Liese et al. |
| 4,836,632 A | 6/1989 | Bardoorian |
| 5,241,184 A | 8/1993 | Menzel |
| 5,518,407 A | 5/1996 | Greenfield et al. |
| 5,622,170 A | 4/1997 | Shulz |
| 5,651,783 A | 7/1997 | Reynard |
| 5,899,692 A | 5/1999 | Davis et al. |
| 6,064,749 A | 5/2000 | Hirota et al. |
| 6,353,226 B1 | 3/2002 | Khalil et al. |
| 6,485,308 B1 | 11/2002 | Goldstein |
| 6,564,087 B1 | 5/2003 | Pitris et al. |
| 6,575,757 B1 | 6/2003 | Leight et al. |
| 6,702,790 B1 | 3/2004 | Ross et al. |
| 6,769,286 B2 | 8/2004 | Biermann et al. |
| 7,383,728 B2 | 6/2008 | Noble et al. |
| 7,500,853 B2 | 3/2009 | Bevirt et al. |
| 7,553,159 B1 | 6/2009 | Arnal et al. |
| 7,594,815 B2 | 9/2009 | Toly |
| 7,665,995 B2 | 2/2010 | Toly |
| 7,725,279 B2 | 5/2010 | Luinge et al. |
| 7,761,139 B2 | 7/2010 | Tearney et al. |
| 7,857,626 B2 | 12/2010 | Toly |
| 8,007,281 B2 | 8/2011 | Toly |
| 8,072,606 B2 | 12/2011 | Chau et al. |
| 8,165,844 B2 | 4/2012 | Luinge et al. |
| 8,203,487 B2 | 6/2012 | Hol et al. |
| 8,208,716 B2 | 6/2012 | Choi et al. |
| 8,250,921 B2 | 8/2012 | Nasiri et al. |
| 8,257,250 B2 | 9/2012 | Tenger et al. |
| 8,277,411 B2 | 10/2012 | Gellman |
| 8,319,182 B1 | 11/2012 | Brady et al. |
| 8,342,853 B2 | 1/2013 | Cohen |
| 8,351,773 B2 | 1/2013 | Nasiri et al. |
| 8,382,485 B2 | 2/2013 | Bardsley |
| 8,450,997 B2 | 5/2013 | Silverman |
| 8,467,855 B2 | 6/2013 | Yasui |
| 8,525,990 B2 | 9/2013 | Wilcken |
| 8,535,062 B2 | 9/2013 | Nguyen |
| 8,632,498 B2 | 1/2014 | Rimsa et al. |
| 8,655,622 B2 | 2/2014 | Yen et al. |
| 8,764,449 B2 | 7/2014 | Rios et al. |
| 8,818,751 B2 | 8/2014 | Van Acht et al. |
| 8,961,189 B2 | 2/2015 | Rios et al. |
| 9,017,080 B1 | 4/2015 | Placik |
| 9,251,721 B2 | 2/2016 | Lampotang et al. |
| 9,443,446 B2 | 9/2016 | Rios et al. |
| 9,792,836 B2 | 10/2017 | Rios et al. |
| 2002/0168618 A1 | 11/2002 | Anderson et al. |
| 2003/0055380 A1 | 3/2003 | Flaherty |
| 2003/0114842 A1 | 6/2003 | DiStefano |
| 2004/0092878 A1 | 5/2004 | Flaherty |
| 2004/0118225 A1 | 6/2004 | Wright et al. |
| 2004/0175684 A1 | 9/2004 | Kaasa et al. |
| 2005/0057243 A1 | 3/2005 | Johnson et al. |
| 2005/0084833 A1 | 4/2005 | Lacey et al. |
| 2005/0181342 A1 | 8/2005 | Toly |
| 2005/0203380 A1* | 9/2005 | Sauer ............. G02B 7/002 600/417 |
| 2006/0084050 A1 | 4/2006 | Haluck |
| 2006/0194180 A1 | 8/2006 | Bevirt et al. |
| 2006/0264745 A1 | 11/2006 | Da Silva |
| 2007/0003917 A1 | 1/2007 | Kitching et al. |
| 2007/0238981 A1 | 10/2007 | Zhu |
| 2008/0097378 A1 | 4/2008 | Zuckerman |
| 2008/0138781 A1 | 6/2008 | Pellegrin et al. |
| 2009/0046140 A1 | 2/2009 | Lashmet |
| 2009/0061404 A1 | 3/2009 | Toly |
| 2009/0081619 A1 | 3/2009 | Miasnik |
| 2009/0081627 A1 | 3/2009 | Ambrozio |
| 2009/0208915 A1 | 8/2009 | Pugh |
| 2009/0263775 A1 | 10/2009 | Ullrich |
| 2009/0265671 A1 | 10/2009 | Sachs et al. |
| 2009/0278791 A1 | 11/2009 | Slycke et al. |
| 2009/0326556 A1 | 12/2009 | Diolaiti |
| 2010/0030111 A1 | 2/2010 | Perriere |
| 2010/0071467 A1 | 3/2010 | Nasiri et al. |
| 2010/0099066 A1 | 4/2010 | Mire et al. |
| 2010/0120006 A1 | 5/2010 | Bell |
| 2010/0167249 A1 | 7/2010 | Ryan |
| 2010/0167254 A1 | 7/2010 | Nguyen |
| 2010/0179428 A1 | 7/2010 | Pederson et al. |
| 2011/0027767 A1 | 2/2011 | Divinagracia |
| 2011/0046915 A1 | 2/2011 | Hol et al. |
| 2011/0071419 A1 | 3/2011 | Liu et al. |
| 2011/0202012 A1 | 8/2011 | Bartlett |
| 2011/0207102 A1 | 8/2011 | Trotta et al. |
| 2011/0236866 A1 | 9/2011 | Psaltis et al. |
| 2011/0269109 A2 | 11/2011 | Miyazaki |
| 2011/0294103 A1 | 12/2011 | Segal et al. |
| 2012/0026307 A1 | 2/2012 | Price |
| 2012/0034587 A1 | 2/2012 | Toly |
| 2012/0130269 A1 | 5/2012 | Rea |
| 2012/0148994 A1 | 6/2012 | Hori et al. |
| 2012/0171652 A1 | 7/2012 | Sparks et al. |
| 2012/0214144 A1 | 8/2012 | Trotta et al. |
| 2012/0219937 A1 | 8/2012 | Hughes |
| 2012/0238875 A1 | 9/2012 | Savitsky et al. |
| 2012/0251987 A1 | 10/2012 | Huang et al. |
| 2012/0280988 A1 | 11/2012 | Lampotang et al. |
| 2012/0282583 A1 | 11/2012 | Thaler et al. |
| 2012/0323520 A1 | 12/2012 | Keal |
| 2013/0018494 A1 | 1/2013 | Amini |
| 2013/0046489 A1 | 2/2013 | Keal |
| 2013/0100256 A1 | 4/2013 | Kirk et al. |
| 2013/0179110 A1 | 7/2013 | Lee |
| 2013/0189658 A1 | 7/2013 | Peters et al. |
| 2013/0197845 A1 | 8/2013 | Keal |
| 2013/0198625 A1 | 8/2013 | Anderson |
| 2013/0203032 A1 | 8/2013 | Bardsley |
| 2013/0267838 A1 | 10/2013 | Fronk et al. |
| 2013/0323700 A1 | 12/2013 | Samosky |
| 2014/0120505 A1 | 5/2014 | Rios et al. |
| 2014/0121636 A1 | 5/2014 | Boyden |
| 2014/0162232 A1 | 6/2014 | Yang et al. |
| 2014/0244209 A1 | 8/2014 | Lee et al. |
| 2014/0260704 A1 | 9/2014 | Lloyd et al. |
| 2014/0278183 A1 | 9/2014 | Zheng et al. |
| 2014/0278205 A1 | 9/2014 | Bhat et al. |
| 2014/0278215 A1 | 9/2014 | Keal et al. |
| 2015/0079545 A1 | 3/2015 | Kurtz |
| 2015/0086955 A1* | 3/2015 | Poniatowski ......... G09B 23/28 434/267 |
| 2015/0206456 A1 | 7/2015 | Foster et al. |
| 2015/0262512 A1 | 9/2015 | Rios et al. |
| 2015/0352294 A1 | 12/2015 | O'Mahony et al. |
| 2016/0000411 A1 | 1/2016 | Raju et al. |
| 2016/0001016 A1 | 1/2016 | Poulsen et al. |
| 2016/0155363 A1 | 6/2016 | Rios et al. |
| 2017/0053563 A1* | 2/2017 | Holloway ............ G09B 23/28 |
| 2017/0136185 A1 | 5/2017 | Rios et al. |
| 2017/0178540 A1 | 6/2017 | Rios et al. |
| 2017/0186339 A1 | 6/2017 | Rios et al. |
| 2017/0245943 A1 | 8/2017 | Foster et al. |
| 2017/0252108 A1 | 9/2017 | Rios et al. |
| 2017/0254636 A1 | 9/2017 | Foster et al. |
| 2017/0316720 A1* | 11/2017 | Singh .................. G09B 23/285 |
| 2018/0225991 A1* | 8/2018 | Pedroso ................ G09B 23/28 |

FOREIGN PATENT DOCUMENTS

| | | |
|---|---|---|
| EP | 1504713 A1 | 2/2005 |
| EP | 1723977 A1 | 11/2006 |
| EP | 1884211 A2 | 2/2008 |
| EP | 2538398 B1 | 8/2015 |
| GB | 2309644 A | 8/1997 |
| GB | 2508510 | 6/2014 |
| WO | WO 02/083003 | 10/2002 |
| WO | WO 2005/083653 | 9/2005 |
| WO | WO 2007/109540 | 9/2007 |
| WO | WO 2009/094646 | 7/2009 |
| WO | WO 2009/141769 | 11/2009 |
| WO | WO 2011/043645 | 4/2011 |

(56) References Cited

FOREIGN PATENT DOCUMENTS

| | | |
|---|---|---|
| WO | WO 2011/127379 | 10/2011 |
| WO | WO 2011/136778 | 11/2011 |
| WO | WO 2012/075166 | 6/2012 |
| WO | WO 2012/101286 | 8/2012 |
| WO | WO 2012/106706 | 8/2012 |
| WO | WO 2012/155056 | 11/2012 |
| WO | WO 2013/025639 | 2/2013 |
| WO | WO 2013/064804 | 5/2013 |
| WO | WO 2014/070799 | 5/2014 |
| WO | WO 2015/109251 | 7/2015 |
| WO | WO 2015/138608 | 9/2015 |
| WO | WO 2016/089706 | 6/2016 |
| WO | WO 2016/162298 | 10/2016 |
| WO | WO 2016/191127 | 12/2016 |
| WO | WO 2017/070391 | 4/2017 |
| WO | WO 2017/151441 | 9/2017 |
| WO | WO 2017/151716 | 9/2017 |
| WO | WO 2017/151963 | 9/2017 |

OTHER PUBLICATIONS

Andraos et al., "Sensing your Orientation" Address 2007, 7 pp.
Arms, S.W., "A Vision for Future Wireless Sensing Systems," 44 pp., 2003.
"B-Smart disposable manometer for measuring peripheral nerve block injection pressures", Bbraun USA, 2016.
Bao, et al. "A Novel Map-Based Dead-Reckoning Algorithm for Indoor Localization", J. Sens. Actuator Networks, 2014, 3, 44-63; doi:10.3390/jsan3010044, 20 pp., Jan. 3, 2014.
Benbasat et al., "An Inertial Measurement Framework for Gesture Recognition and Applications," I. Wachsmuth and T. Sowa (Eds.): GW 2001, Springer-Verlag Berlin Heidelberg, 12 pp., 2002.
Bergamini et al., "Estimating Orientation Using Magnetic and Inertial Sensors and Different Sensor Fusion Approaches: Accuracy Assessment in Manual and Locomotion Tasks", Oct. 2014, 18625-18649.
Brunet et al., "Uncalibrated Stereo Vision," A CS 766 Project, University of Wisconsin—Madison, 6 pp, Fall 2004, http://pages.cs.wisc.edu/~chaol/cs766/.
Brunet et al., "Uncalibrated Stereo Vision," A CS 766 Project, University of Wisconsin—Madison, 13 pp, Fall 2004, http://pages.cs.wisc.edu/~chaol/cs766/.
Desjardins, et al. "Epidural needle with embedded optical fibers for spectroscopic differentiation of tissue: ex vivo feasibility study", Biomedical Optics Express, vol. 2(6): pp. 1-10. Jun. 2011.
"EPGL Medical Invents Smart Epidural Needle, Nerve Ablation and Trigger Point Treatment Devices: New Smart Medical Devices Will Give Physicians Advanced Situational Awareness During Critical Procedures," EPGL Medical, dated Aug. 12, 2013, in 3 pages. Retrieved from http://www.prnewswire.com/news-releases/epgl-medical-invents-smart-epidural-needle-nerve-ablation-and-trigger-point-treatment-devices-219344621.html#.
"The EpiAccess System: Access with Confidence", EpiEP Epicardial Solutions, dated 2015, in 2 pages.
Esteve, Eric, "Why do you need 9D Sensor Fusion to support 3D orientation?", 5 pp., Aug. 23, 2014, https://www.semiwiki.com/forum/content/3794-why-do-you-need-9d-sensor-fusion-support-3d-orientation.html.
Grenet et al., "spaceCoder: a Nanometric 3D Position Sensing Device," CSEM Scientific & Technical Report, 1 page, 2011.
Helen, L., et al. "Investigation of tissue bioimpedance using a macro-needle with a potential application in determination of needle-to-nerve proximity", Proceedings of the 8th International Conference on Sensing Technology, Sep. 2-4, 2014, pp. 376-380.
Inition. Virtual Botox: Haptic App Simulated Injecting the Real Thing. Retrieved from http://inition.co.uk/case-study/virtual-botox-haptic-app-simulates-injecting-real-thing.
Kalvøy, H., et al., "Detection of intraneural needle-placement with multiple frequency bioimpedance monitoring: a novel method", Journal of Clinical Monitoring and Computing, Apr. 2016, 30(2):185-192.
Madgwick, Sebastian O.H., "An efficient orientation filter for inertial and inertial/magnetic sensor arrays," 32 pp., Apr. 30, 2010.
Microsoft, "Integrating Motion and Orientation Sensors," 85 pp., Jun. 10, 2013.
Miller, Nathan L., Low-Power, Miniature Inertial Navigation System with Embedded GPS and Extended Kalman Filter, MicroStrain, Inc., 12 pp., 2012.
MPU-9150 9-Axis Evaluation Board User Guide, Revision 1.0, 15 pp., May 11, 2011, http//www.invensense.com.
MPU-9150, Register Map and Descriptions, Revision 4.2, 52 pp., Sep. 18, 2013, http//www.invensense.com.
MPU-9150, Product Specification, Revision 4.3, 50 pp., Sep. 18, 2013, http://www.invensense.com.
PST Iris Tracker, Plug and Play, 3D optical motion tracking specifications, 1 p., Dec. 4, 2014, www.pstech.com.
PST Iris Tracker, Instruction Manual, 3D optical motion tracking specifications, 42 pp., Jul. 27, 2012, www.pstech.com.
Struik, Pieter, "Ultra Low-Power 9D Fusion Implementation: A Case Study," Synopsis, Inc., 7 pp., Jun. 2014.
Sutherland, et al. "An Augmented Reality Haptic Training Simulator for Spinal Needle Procedures," IEEE, 2011.
Varesano, Fabio, "Prototyping Orientation and Motion Sensing Objects with Open Hardware," Dipartimento di Informatica, Univ. Torino, http://www.di.unito.it/~varesano, Feb. 10, 2013, 4 pp.
Varesano, Fabio, "FreeIMU: An Open Hardware Framework for Orientation and Motion Sensing," Dipartimento di Informatica, Univ. Torino, http://www.di.unito.it/~varesano, Mar. 20, 2013, 10 pp.

* cited by examiner

SUTURE TECHNIQUE TRAINING SYSTEM

INCORPORATION BY REFERENCE TO ANY PRIORITY APPLICATIONS

This application claims priority benefit of U.S. Provisional Application No. 62/444,483, filed Jan. 10, 2017, titled "Suture Technique Training System," the entirety of which is hereby incorporated by reference herein.

Any and all applications for which a foreign or domestic priority claim is identified in the Application Data Sheet as filed with the present application are hereby incorporated by reference under 37 C.F.R. § 1.57.

BACKGROUND

Field

The present disclosure generally relates to a suture apparatus and training system for development and evaluation of suturing skills by clinical professionals.

Description of the Related Art

Suturing is a common method of closing lacerations, incisions, lesions, and the like. However, poor suturing technique can have functional and cosmetic consequences. For example, poor suturing technique can adversely affect wound healing and scarring. Suture tension can also change the anatomical contours of the skin.

Synthetic models exist for clinical professionals to practice suturing techniques, but provide no feedback on the accuracy of the suturing.

SUMMARY

The training systems disclosed herein can be used to educate, train, and certify medical personnel for suturing procedures, including, for example, a testing program for certifying medical personnel. The training systems disclosed herein can provide feedback on trainees and the accuracy of suture procedures performed, and in some instances, in real-time. These training systems will enable users to practice a variety of suturing techniques prior to performing live suturing procedures and reduce the risks associated with inexperienced and uncertified medical personnel performing suture procedures. These training systems also eliminate the need to find live models for hands-on training sessions.

Some aspects of the present disclosure are directed toward a system for training clinicians to perform suturing procedures. The system can include a training tool, a training apparatus, a three-dimensional tracking system, and a processing unit. The training tool can include at least one light-reflective marking. The training apparatus can be representative of an anatomical structure and configured to receive the training tool. The three-dimensional tracking system can include a light emitter positioned in an internal portion of the training apparatus. The light emitter can be configured to illuminate the at least one light-reflective marking on the training tool when the training apparatus receives the training tool. The three-dimensional tracking system can also include one or more light detectors positioned in the internal portion of the training apparatus. The light detectors can be configured to detect light reflected by the at least one light-reflective marker of the training tool. The light detectors, can be, for example, one or more cameras positioned at different locations internal to the training apparatus. The processing unit can be configured to receive and process an indication of the detected light from the one or more light detectors to determine one or more training parameters, including, for example, location and depth.

Some aspects of the present disclosure are directed toward a method of training clinicians to perform suturing procedures. The method can include suturing a training apparatus representative of an anatomical structure using a training tool. The training tool can include a needle, a suturing material, and at least one light-reflective marking. The method can also include tracking the training tool by detecting light reflected from the tracking tool during suturing, and processing the detected light to determine one or more training parameters.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

The training systems disclosed herein can be used to educate, train, and certify medical personnel for suturing procedures. As described in greater detail below, the training systems disclosed herein can track one or more light reflective markers on a training tool, including for example one or more needles and/or suturing material, to assess the accuracy and quality of a user's suturing technique. The training system can include a three-dimensional tracking system to monitor light that reflects off the one or more light reflective processor. The data from the three-dimensional tracking system can be processed to determine or evaluate one or more suturing technique parameters, including but not limited to, a user's suturing motion, depth of needle or suture penetration, location of needle penetration, location of sutures, movement of sutures, etc. These one or more parameters can be output to an output device to provide real-time feedback to the user or other personnel on the accuracy or quality of the user's suturing technique. For certifying purposes, the one or more parameters could be compared to a baseline to determine whether the user passed.

Figure 1:
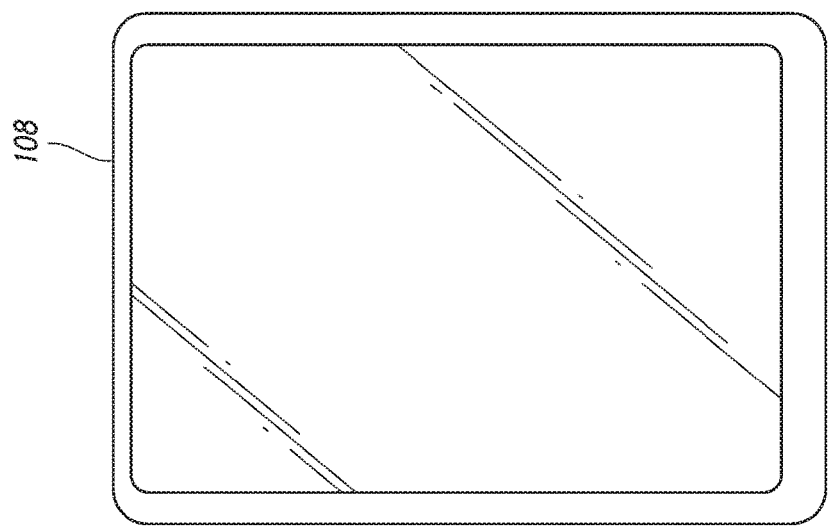
FIG. 1 illustrates a of a suture training system.
Figure 1:
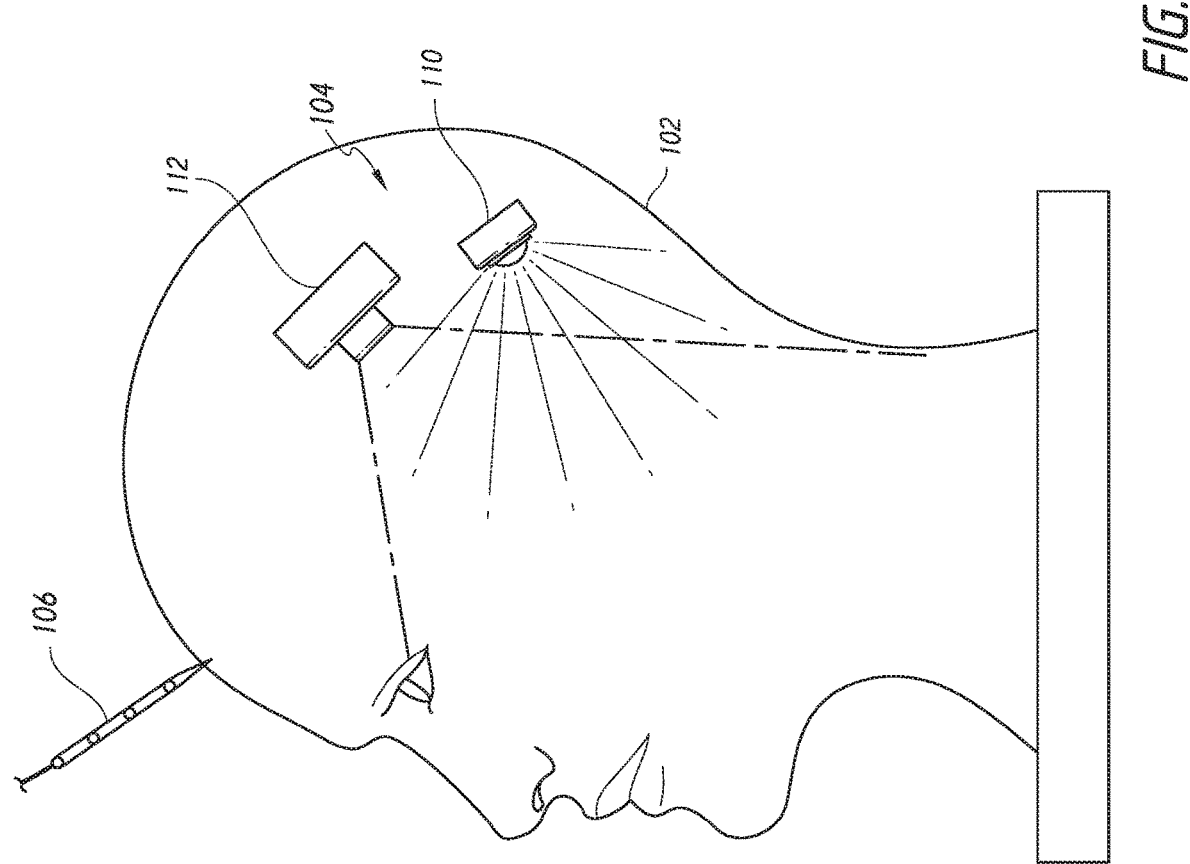

FIG. 1 illustrates a suture technique training system 100, which can include: a training apparatus 102, a three-dimensional tracking system 104 associated with the training apparatus 102, a training tool 106, a processing unit, and an output device 108.

Figure 2:
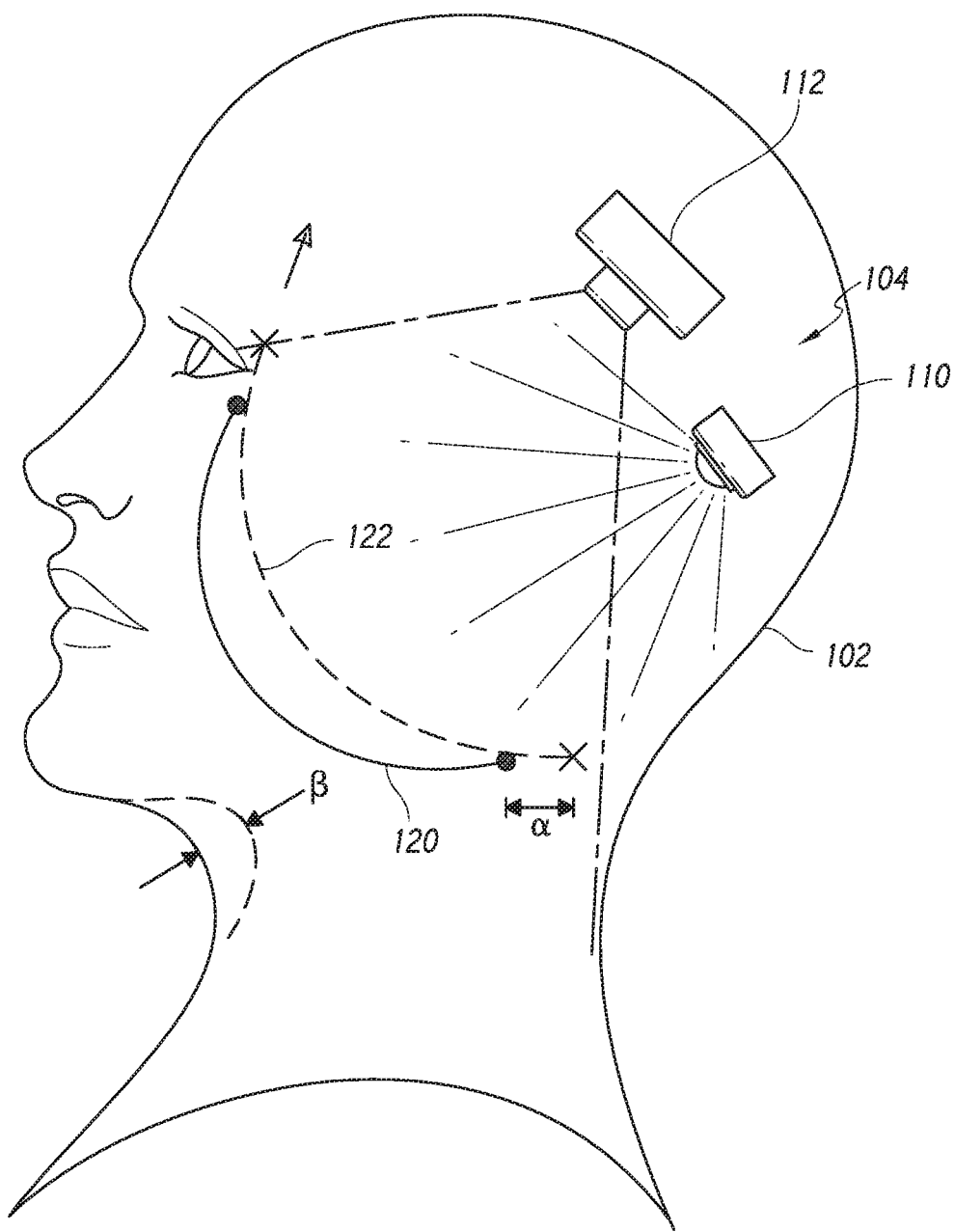
FIG. 2 illustrates the training apparatus shown in FIG. 1 with a suture under tension.

FIG. 2 shows a training apparatus 102 having an anatomically correct model of an animal or animal body part. As illustrated, the training apparatus 102 represents a human head and neck. The training apparatus 100 can include any of the features of the injection apparatuses described in U.S. Pat. No. 8,764,449, titled "System for Cosmetic and Therapeutic Training," issued Jul. 1, 2014, which is hereby incorporated by reference in its entirety herein.

The training apparatus 102 can include one or more layers of artificial material to represent muscle, flesh tissue, hair, and/or scales. The one or more layers can include the same or different levels of transparency (for example, opaque, tinted, marked, and/or clear), color, coarseness, thickness, stiffness, and/or density. Materials used for the muscle, flesh, and skin may include, without limitation, silicone, rubber, polyurethane, or other such materials that are suitable to simulate the structure and characteristics of the tissue being simulated by the training apparatus. The one or more of these layers can be removable and/or replaceable. The training apparatus 102 can be reusable or disposable.

As an example, the training apparatus 102 can include a clear artificial material covered by an opaque synthetic material to represent skin.

As another example, the base layer of the training apparatus 102 can include a clear plastic shell simulating a human or animal body part, such as, for example, a human or animal head. The clear plastic shell can be covered with layer(s) of elastomer membranes simulating human or animal muscle and/or skin. The top layer of skin can include separate layers simulating mammalian skin: the epidermis, dermis, and hypodermis. The layers of skin can be thicker or thinner to simulate the skin of humans or animals with uneven skin layers or damaged skin.

The different removable layers of the training apparatus 102 can be embedded with sensors (not shown) that can be activated when contacted by the training tool 106. For example, the training tool 106 could be light emitting, sound emitting, magnetic flux emitting, radio frequency emitting, or otherwise. The sensors embedded in the training apparatus 102 can detect the emission to provide a three-dimensional position a tip of the training tool 106.

The suture training system 100 can also include a three-dimensional tracking system 104 configured to capture three-dimensional positional data of the training tool 106. As shown in FIG. 2, the three dimensional tracking system 104 can be positioned in an interior portion of the training apparatus 102. However, for other anatomical models, the three-dimensional tracking system 104 can be positioned external to the training apparatus 102. Components of the three-dimensional tracking system 104 can be mounted to the training apparatus 102 or free standing within the training apparatus 102.

The three-dimensional tracking system 104 can include a light emitter 110 and a light detector 112 (for example, optical sensor, camera, or otherwise). When the light detector 112 is positioned within the training apparatus 102, at least an internal surface of the training apparatus 102 is transparent to the emitted light. When the light detector 112 is positioned external to the training apparatus 102, at least an outer surface of the training apparatus 102 is transparent to the emitted light. Although the embodiments described herein are with respect to light, other detection means are possible, including but not limited to, sound, magnetic flux, radiofrequency, or otherwise.

The light emitter 110 may include one or more LEDs, laser diodes, or any other light emitting device or combination of devices. The light source can emit light along a spectrum of visible light. The light source can also or alternatively emit non-visible light, such as infrared light. Moreover, the light detector 112 can be configured to detect visible and/or non-visible light. The light detector 112 can communicate a raw or processed output to a processing unit or an output device 108.

As illustrated in FIG. 2, the three-dimensional tracking system 104 can be positioned such that the tracking system's 104 field-of-view covers a portion of the training apparatus on which suturing training may be performed. The three-dimensional tracking system 104 is configured to track the position and orientation of the training tool 106 during the suturing training procedure.

Although FIG. 2 illustrates a single light detector 112, the tracking system 104 could include more than one light detector 112 positioned at different locations and/or with different viewing axes. For example, the tracking system 104 could be implemented as a stereoscopic sensor pair. As another example, a first light detector could be oriented such that the viewing axis extends in an anterior and/or inferior direction. The viewing axis of a second light detector could extend in a different direction, for example, in a posterior and/or inferior direction. In configurations with more than one light detector 112, the light detectors may have overlapping or discrete fields-of-view. The light detectors 112 could be positioned to maximize the overlapping field of view in the region of most expected suturing. The positioned and/or angles of the light detectors may be adjustable to change the field-of-view.

The three-dimensional tracking system 104 can send the detected tracking information to a processing unit. The processing unit can be positioned in an interior portion of the training apparatus 102 or remote from the training apparatus 102. For example, the processing unit could be positioned in the interior portion of the training apparatus 102, as a part of the three-dimensional tracking system 104 or as separate component. Alternatively, the processing unit could be remote from the training apparatus 102, for example, in an output device 108. Based on the positional data, the processing unit can determine an indication of one or more suture parameters. The processing unit can also collect the information for use in data gathering or informatics.

The processing unit can communicate the one or more suture parameters to the output device 108, which can display the results received from a suturing procedure. The output device 108 can include any type of display useful to a user, such as, for example, a tablet, phone, laptop or desktop computer, television, projector or any other electronic or paper-based display technology. The output device 108 can also include lights, graphical displays, audio devices, or user controls. The output device 108 can be an electronic, computer, or mobile device, for example, a smart phone or a tablet.

If the output device 108 includes the processing unit, in some examples, the output device 108 can run a dedicated application configured to receive wireless or wired communication directly from the three-dimensional tracking system 104 and analyze this information for feedback and display to a user. Alternatively, a separate processing unit in the training apparatus 102 can process the information before sending the processed information to the output device 108 for display.

Figure 3:
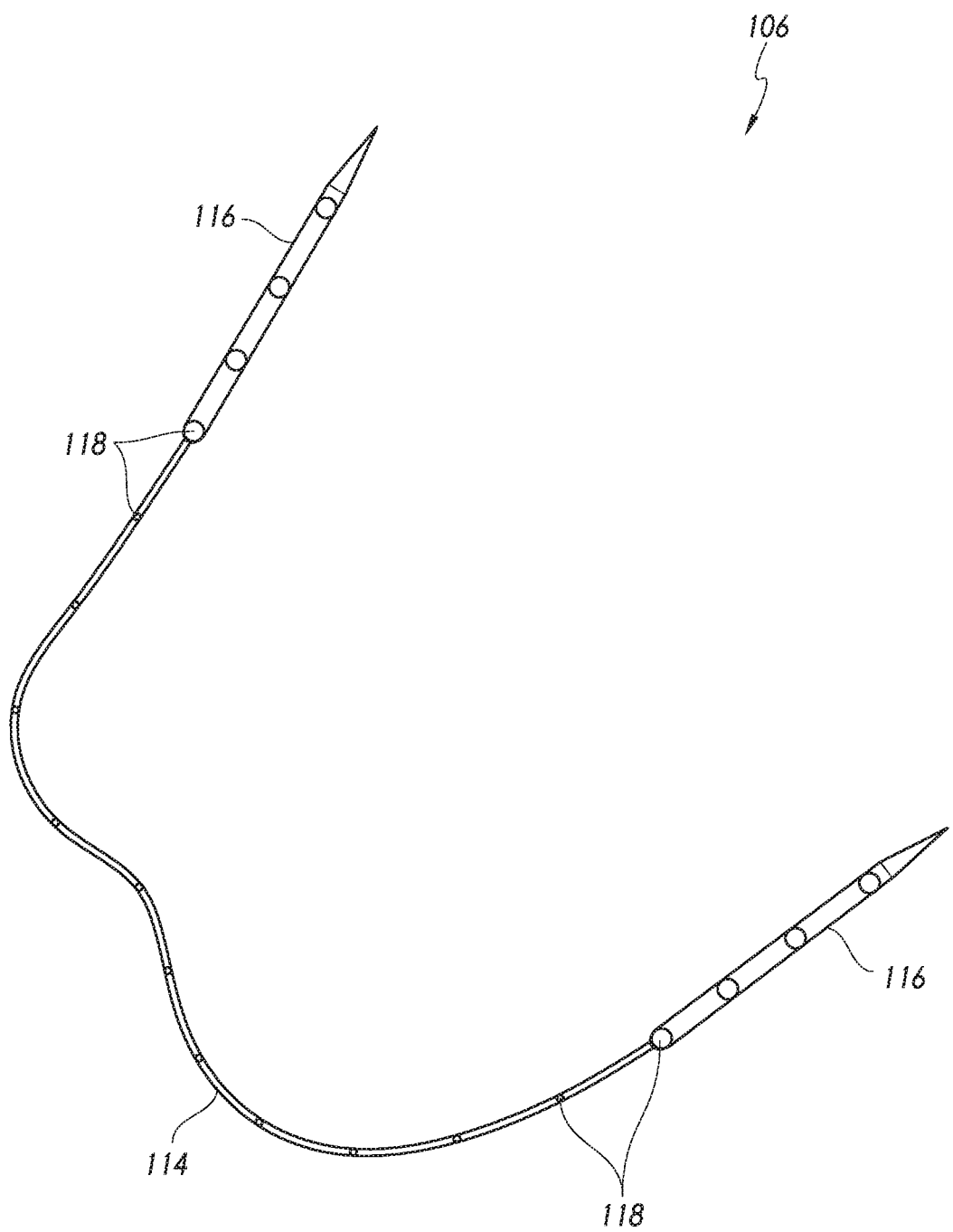
FIG. 3 illustrates the training tool shown in FIG. 1.

FIG. 3 illustrates a training tool 106 including suture material 114 attached to one or more suture needles 116. The suturing material 114 may be a compliant material. The suture needle 116 may be a rigid structure and may be straight, curved, hooked, or any other form that can be used to suture anatomical structures. The training tool 106 can be of any size or shape that may be used to simulate a suturing procedure.

The suture needle 116 and/or suturing material 114 can include one or more luminescent, fluorescent, or other light-reflecting markings 118. For example, the light-reflecting structures can include dots, crosses, hash marks, or other patterns, spaced along the suture needle 116 and/or suturing material 114.

In use, the needle 116 of the training tool 106 passes through the clear artificial flesh of the training apparatus 102 and draws the suturing material 114 behind it. The needle 116 and the suturing material 114 are visible to the three-dimensional tracking system 104 positioned in an interior portion of training apparatus 102. The light emitted from the light emitter 110 is directed to the training tool 106 and is reflected by the luminescent, fluorescent, or otherwise light-reflecting markings 118 on the training tool 106. The reflected light is detected by light detector 112. This information detected by the three-dimensional tracking system 104 can be processed and communicated to an output device 108 for testing or certification purposes. As an example, the three-dimensional tracking information generated by the three-dimensional tracking system 104 may be processed to create a representation of the suturing motion of the training tool 106, for example a graphical representation. As another example, the captured tracking data may be processed to provide information about the suturing activity, including but not limited to, location with respect to the anatomy, depth of penetration into tissue, tension force applied to the sutured tissue or suturing material, and/or other related features.

FIG. 2 illustrates how a suture can move from a first position 120 to a second position 122 depending on the amount of suture tension. Even if the location of the sutures is initially proper, suture tension can cause undesirable movement of the sutures, which can change the anatomical contours of the skin. Thus, the training system 100 also provides a method of tracking the suture tension.

Figure 4:
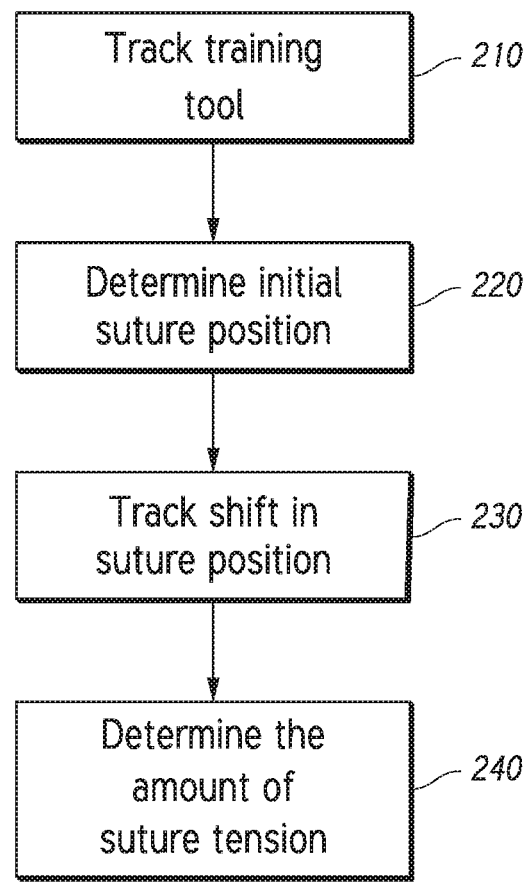
FIG. 4 is a flow chart showing a method of determining suture tension.

As shown in FIG. 4, the three-dimensional tracking system tracks the training tool 106 as it penetrates the training apparatus 102 (block 210). Based on the location where the training tool 106 penetrates training apparatus 102, the training system 100 can determine and store an initial suture position 120 (block 220). As the suturing training procedure progresses, the position of the suturing material 114 may shift to a different position 122 as tension is applied to the anatomical structures of the training apparatus 102. The three-dimensional tracking system 104 can track the change in suture position a (block 230). Based on the change in suture position a, the processing unit can determine the amount of suture tension or tension applied to the flesh. The three-dimensional system 104 may also track and evaluate the tension applied to the suturing material 114 by, for example, tracking a change in position β of the surface of the flesh as the suture tension changes.

Although the illustrated embodiment shows an anatomical model of the human head, the training apparatus can simulate any human or animal part, such as, for example, the face, head, brain, neck, back, chest, spine, torso, arms, legs, hands, feet, mouth, or any other body part, including internal organs, or portion of the body of interest. The training apparatus may also simulate different bones or organs of the human or animal body, such as the heart, brain, or liver, that require attention during suturing procedures. The bones or organs can be placed within an anatomically correct model of a simulated human or animal body part. The training apparatus may also simulate a human or animal mouth for dental or periodontal suturing procedures.

Although the present disclosure specifically describes the use of a light detector to capture three-dimensional positional data, it is to be understood that the principles disclosed throughout the present disclosure may also apply to any three-dimensional tracking system.

The methods disclosed herein may include certain actions taken by a clinical practitioner; however, the methods can also include any third-party instruction of those actions, either expressly or by implication. For example, actions such as "suturing" include "instructing suturing."

The methods, processes, routines, or algorithms described herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it can be understood that various omissions, substitutions, and changes in the form and details of the devices or algorithms can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A system for training clinicians to perform suturing procedures, the system comprising:
    a training tool comprising at least one light-reflective marking;
    a training apparatus representative of an anatomical structure and configured to receive the training tool;
    a light emitter positioned in an internal portion of the training apparatus, the light emitter configured to illuminate the at least one light-reflective marking on the training tool when the training apparatus receives the training tool; and
    a light detector positioned in the internal portion of the training apparatus, the light detector configured to detect light reflected by the at least one light-reflective marker of the training tool; and
    a processing unit configured to receive and process an indication of the detected light from the light detector to determine one or more training parameters.

2. The system of claim 1, wherein the training tool comprises a needle.

3. The system of claim 2, wherein the needle comprises the at least one light-reflective marking.

4. The system of claim 2, wherein the training tool comprises a suturing material.

5. The system of claim 4, wherein the suturing material comprises the at least one light-reflective marking.

6. The system of claim 1, wherein the one or more training parameters comprises a location of the training tool.

7. The system of claim 1, wherein the one or more training parameters comprises a depth of penetration.

8. The system of claim 1, wherein the one or more training parameters comprises a tension force applied to the training tool.

9. The system of claim 1, the processing unit is configured to receive and process indications of the detected light from the light detector and generate a representation of a path of the training tool.

10. The system of claim 1, further comprising an output device configured to display the one or more training parameters.

11. The system of claim 1, wherein the processing unit is in the interior portion of the training apparatus.

12. The system of claim 1, wherein the processing unit is remote from the training apparatus.

13. The system of claim 1, wherein the light emitter emits visible light.

14. The system of claim 1, wherein the light emitter emits non-visible light.

15. A method of training clinicians to perform suturing procedures, the method comprising:
    suturing a training apparatus representative of an anatomical structure using a training tool, the training tool comprising:
        a needle;
        a suturing material; and
        at least one light-reflective marking;
    tracking the training tool by detecting light reflected from the tracking tool during suturing; and
    processing the detected light to determine one or more training parameters.

16. The method of claim 15, further comprising determining an accuracy of the suturing based on the one or more training parameters.

17. The method of claim 15, further comprising generating a representation of a path of the testing tool based on the one or more training parameters.

18. The method of claim 15, further comprising outputting the one or more training parameters to a display device.

19. The method of claim 15, further comprising determining a change in position of the suturing material during suturing by tracking at least one light reflective marking on the suturing material.

20. The method of claim 19, further comprising determining a tension force applied to the training apparatus based on the change in position of the suturing material.

* * * * *